United States Patent [19]
Lee et al.

[11] Patent Number: 6,146,641
[45] Date of Patent: Nov. 14, 2000

[54] AVIAN LEUKOSIS VIRUS SUBGROUP J ENVELOPE GENE PRODUCT FOR DIAGNOSIS AND IMMUNOGENIC COMPOSITION

[75] Inventors: Lucy F. Lee, East Lansing; Aly M. Fadly; Henry D. Hunt, both of Okemos, all of Mich.

[73] Assignee: The United States of America as represented by the Secretary of Agriculture, Washington, D.C.

[21] Appl. No.: 09/160,065

[22] Filed: Sep. 24, 1998

Related U.S. Application Data

[60] Provisional application No. 60/093,632, Jul. 21, 1998.
[51] Int. Cl.$^7$ .......................... A61K 39/12; A61K 39/21; C12N 15/00
[52] U.S. Cl. ..................... 424/199.1; 424/204.1; 424/207.1; 435/320.1; 435/235.1; 530/300; 530/350; 536/23.72
[58] Field of Search .............................. 424/199.1, 204.1, 424/207.1, 816; 435/320.1, 235.1; 536/23.72; 530/350, 300

[56] References Cited

PUBLICATIONS

Venugopal, K., et al., "Antigenic variants of J subgroup avian leukosis virus: sequence analysis reveals multiple changes in the env gene", *Journal of General Virology*, 2998, 79, pp. 757–766, 1998.

Venugopal, K., et al., "Recombinant env–gp85 of HRS–103 (Subgroup J) Avian Leukosis Virus:Antigenic Characteristics and Usefulness as a Diagnostic Reagent", *Avian Diseases*, 41, 1997, pp. 283–288.

Fadly, A. M., et al., "Some Characteristics of a Subgroup J–Like Avian Leukosis Virus Isolated from Broiler Breeder Chickens in the United States", Abstract, Aug. 18–22, 1997, Budapest Hungary, XIth International Congress of the World Veterinary Poultry Association.

Fadly, A.M., et al,, "An Overview of Subgroup J–Like Avian Leukosis Virus Infection in Broiler Breeder Flocks in the United States", Abstract, Avian Tumor Viruses Symposium, Jul. 24, 1997, 40th Annual Meeting, Reno, Nevada, American Association of Avian Pathologists.

Fadly, Aly M., "Elocytomatosis: An Emerging Disease of Broiler Breeder Chickens", Abstract, Proceedings of the Forty–Seventh Western Poultry Disease Conference, Mar. 8–10, 1998, Sacramento, CA.

Bai, J., et al., "Sequence of host–range determinants in the env of a full–length, infectious proviral clone of exogenous avian leukosis virus HPRS–103 confirms that it represents a new subgroup (designated J)", *Journal of General Virology*, 1995, 76, pp. 181–187.

Bai, J., et al., "HPRS–103 (Exogenous Avian Leukosis Virus, Subgroup J) Has an env Gene Related to Those of Endogenous Elements EAV–O and E51 and an E Element Found Previously Only in Sarcoma Viruses", *Journal of Virology*, Feb. 1995, vol. 69, No. 2, pp. 779–784.

*Primary Examiner*—Ali Salimi
*Attorney, Agent, or Firm*—M. Howard Silverstein; Curtis P. Ribando; John D. Fado

[57] ABSTRACT

The envelope (env) gene from avian leukosis virus subgroup J (ALV-J) strain Hc1 has been isolated, sequenced and cloned into an expression vector. The ALV-J Hc1 env gene and expressed protein are useful for development of diagnostic assays to detect Hc1-specific nucleic acid and proteins and for eliciting an immune response in chickens.

8 Claims, 9 Drawing Sheets

Fig. 4A

```
GCA AAA TGG AAA AGT GAT GAC CCT CTT ATA AGG CCC TAT GTC AAC CAA TCA TGG ACG ATG GTA AGT CCA
 A   K   W   K   S   D   D   P   L   I   R   P   Y   V   N   Q   S   W   T   M   V   S   P
                                                                 8                         759
ATA AAC ACA GAG AGT TTT TCA ATA AGT AGA TGT GGA TTC ACC AGC AAT GAG ACT CGT TAT TAT
 I   N   T   E   S   F   S   I   S   R   C   G   F   T   S   N   E   T   R   Y   Y
                                                                     9                     828
AGA GGG AAC TTT TCT AAT TGG TGT GGT TCA AAA GGG TCA GCG TAC GGA TAT AGT AAT GGG ACA
 R   G   N   F   S   N   W   C   G   S   K   G   S   A   Y   G   Y   S   N   G   T
             10                                                              11            897
GAA TGT TCC GAT GGC ACG GGT TGC GGT AAT TGG AAA GCA GAA TGG AAG GCA CTT CCC CCA TAT GCA TAT GGG
 E   C   S   D   G   T   G   C   G   N   C   T   A   E   W   K   A   L   P   P   Y   A   Y   G
                                 12                                                         966
TTT ACC TTC GGG AAT GGG GGT TGC GGT ATA GAG CCA GAG ATT CTG AAT GGG ACT AAT GCC CTC CCC CCA GGT ATT
 F   T   F   G   N   G   G   C   G   I   E   P   E   I   L   N   G   T   N   A   L   P   P   G   I
                                                     13                                    1035
TTC TTG ATT TGT GGG GAC AGG AGG GCT TGG CAA GGT CGT AGT AAT CCG ATC CCG AGT TGG GGA CCC TGT TAT CTA
 F   L   I   C   G   D   R   R   A   W   Q   G   R   S   N   P   I   P   S   W   G   P   C   Y   L
                                                                                            1104
GGA CAA TTG ACT ATG CTC TCT CCT AAC TTT ACC ACC TGG ATA ACA TAT GGG CCG AAC ATT ACG GGT CAC
 G   Q   L   T   M   L   S   P   N   F   T   T   W   I   T   Y   G   P   N   I   T   G   H
                             14                                              15            1173
CGC CGT AGC AGG CGG ATA TTT GCT TCT TCG CTG AGT CGT CTC TCA GTT CCT GAT GAG CTA TGG AGT GTG
 R   R   S   R   R   I   F   A   S   S   L   S   R   L   S   V   P   D   E   L   W   S   V
         gp37                                                                               1242
ACA GCC CGG ATA TTT GCT TCT TTC TTT GCT CCT GGT GTA GCA GCA CAA GCC TTA AAG GAG ATT GAA
 T   A   R   I   F   A   S   F   F   A   P   G   V   A   A   Q   A   L   K   E   I   E
                                                                                            1311

Fig. 4B
```

```
CGC TTG GCA TGT TGG TCG GTT AAG CAA GCG AAT TTA ACA TCA TTA ATA TTG AAT GCG ATG CTG GAG GAC
 R   L   A   C   W   S   V   K   Q   A   N   L   T   S   L   I   L   N   A   M   L   E   D  1380
                                         16
ATG AAC AGC ATC CGG CAC GCG GTG TTG CAG AAT CGA GCA GCC ATC GAT TTC TTA CTC CTG GCG CAA GGA
 M   N   S   I   R   H   A   V   L   Q   N   R   A   A   I   D   F   L   L   L   A   Q   G  1449
CAC GGG TGT CAA GAC GTG GAA GGG ATG TGT TTC AAT CTC AGC GAT CAC AGT GAG TCC ATT CAC AAG
 H   G   C   Q   D   V   E   G   M   C   F   N   L   S   D   H   S   E   S   I   H   K  1518
                                                        17
GCG CTT CAA GCC ATG AAG GAA CAT ACA GAG AAG ATA CGG GAA GAT CCC ATA GGG GAT TGG TTT
 A   L   Q   A   M   K   E   H   T   E   K   I   R   E   D   P   I   G   D   W   F  1587
ACG CGC ACG TTT GGT GGT CTT GGA GGG TGG CTC GCA AAA GGC GTT AAG ACG CTA CTG TTT GCC TTG CTT
 T   R   T   F   G   G   L   G   G   W   L   A   K   G   V   K   T   L   L   F   A   L   L  1656
GTC ATA GTC TGT CTA TTA GCT ATC ATT CCA TGT ATA AGA TAT CAT AGA TAC CGC ATA TCG AGA ACA
 V   I   V   C   L   L   A   I   I   P   C   I   K   C   F   Q   D   C   L   S   R   T  1719
ATG TAT CAG CTT ATG GAT GAA CGC AGA ATT AGG GAG CAG CTG TAG GTC GAC
 M   Y   Q   L   M   D   E   R   R   I   R   E   Q   L   *
```

Fig. 4C

SEQUENCE LISTING

<160> NUMBER OF SEQ ID NOS: 6

<210> SEQ ID NO 1
<211> LENGTH: 1719
<212> TYPE: DNA
<213> ORGANISM: Avian leukosis virus
<220> FEATURE:
<221> NAME/KEY: CDS
<222> LOCATION: (7)..(1710)

<400> SEQUENCE: 1 ggatcc atg gaa gcg gtc ata aag gca ttt cta act ggg cac cct gga 48
Met Glu Ala Val Ile Lys Ala Phe Leu Thr Gly His Pro Gly
1 5 10 aag gtg agc aag aag gac tct aag aag aag ccg cca gca aca agc aag 96
Lys Val Ser Lys Lys Asp Ser Lys Lys Lys Pro Pro Ala Thr Ser Lys
15 20 25 30 aaa gac ccg gag aag aca ccc ttg ctg cca tcg aga ggt tac ttc ttc 144
Lys Asp Pro Glu Lys Thr Pro Leu Leu Pro Ser Arg Gly Tyr Phe Phe
35 40 45 ttc caa atg ata ctt gtg tgc gtg gtt att att tcc gtg gtc cca ggg 192
Phe Gln Met Ile Leu Val Cys Val Val Ile Ile Ser Val Val Pro Gly
50 55 60 gtg ggg gga gtt cat ctg ttg caa caa cca gga aac gtg tgg gtc acc 240
Val Gly Gly Val His Leu Leu Gln Gln Pro Gly Asn Val Trp Val Thr
65 70 75 tgg gca aat aag acg ggc cga aca gat ttt tgc ctt agt tta cag tca 288
Trp Ala Asn Lys Thr Gly Arg Thr Asp Phe Cys Leu Ser Leu Gln Ser
80 85 90 gcg acc tca cca ttc cgc acc tgc ttg ata ggc att cca cag tat cct 336
Ala Thr Ser Pro Phe Arg Thr Cys Leu Ile Gly Ile Pro Gln Tyr Pro
95 100 105 110 ctg agc acc ttt gag gga tat gtc act aat gtt act gct tgc gat aac 384
Leu Ser Thr Phe Glu Gly Tyr Val Thr Asn Val Thr Ala Cys Asp Asn
115 120 125 agc gcc gat tta gcc aac caa aca gca tgc ttg ata aag gct cta aat 432
Ser Ala Asp Leu Ala Asn Gln Thr Ala Cys Leu Ile Lys Ala Leu Asn
130 135 140

-continued

```
aca acc ctc cct tgg gac ccc caa gaa tta gat att tta ggg tcc cag         480
Thr Thr Leu Pro Trp Asp Pro Gln Glu Leu Asp Ile Leu Gly Ser Gln
            145                 150                 155 atg atc aag aac gga aca aaa cgt acg tgt gtt acc ttt ggt tcg gtg         528
Met Ile Lys Asn Gly Thr Lys Arg Thr Cys Val Thr Phe Gly Ser Val
    160                 165                 170 tgc tat aaa gag gac aat agt aca gtc tgt cac aat ttt gat ggg aat         576
Cys Tyr Lys Glu Asp Asn Ser Thr Val Cys His Asn Phe Asp Gly Asn
175                 180                 185                 190 ttt aat ggg act ggt ggg gcg gaa gca gaa ttg cgt gac ttc ata gca         624
Phe Asn Gly Thr Gly Gly Ala Glu Ala Glu Leu Arg Asp Phe Ile Ala
                195                 200                 205 aaa tgg aaa agt gat gac cct ctt ata agg ccc tat gtc aac caa tca         672
Lys Trp Lys Ser Asp Asp Pro Leu Ile Arg Pro Tyr Val Asn Gln Ser
            210                 215                 220 tgg acg atg gta agt cca ata aac aca gag agt ttt tca ata agt agt         720
Trp Thr Met Val Ser Pro Ile Asn Thr Glu Ser Phe Ser Ile Ser Ser
        225                 230                 235 aga tat tgt gga ttc acc agc aat gag act cgt tat tat aga ggg aac         768
Arg Tyr Cys Gly Phe Thr Ser Asn Glu Thr Arg Tyr Tyr Arg Gly Asn
    240                 245                 250 ttt tct aat tgg tgt ggt tca aaa ggg gga aaa tgg tca gcg gga tac         816
Phe Ser Asn Trp Cys Gly Ser Lys Gly Gly Lys Trp Ser Ala Gly Tyr
255                 260                 265                 270 agt aat ggg aca gaa tgt tcc gat ggc acg gcg ggt tgc ggt ggt aat         864
Ser Asn Gly Thr Glu Cys Ser Asp Gly Thr Ala Gly Cys Gly Gly Asn
                275                 280                 285 tgc aca gcg gaa tgg aat tat tat gca tat ggg ttt acc ttc ggg aat         912
Cys Thr Ala Glu Trp Asn Tyr Tyr Ala Tyr Gly Phe Thr Phe Gly Asn
            290                 295                 300 aag cca gag ata ttg tgg aat aat ggg act gct aag gca ctc ccc cca         960
Lys Pro Glu Ile Leu Trp Asn Asn Gly Thr Ala Lys Ala Leu Pro Pro
        305                 310                 315 ggt att ttc ttg att tgt ggg gac agg gct tgg caa ggt atc ccg agt        1008
Gly Ile Phe Leu Ile Cys Gly Asp Arg Ala Trp Gln Gly Ile Pro Ser
    320                 325                 330 aat gcc ttg gga ggg ccc tgt tat cta gga caa ttg act atg ctc tct        1056
Asn Ala Leu Gly Gly Pro Cys Tyr Leu Gly Gln Leu Thr Met Leu Ser
335                 340                 345                 350 cct aac ttt acc acc tgg ata aca tat ggg ccg aac att acg ggt cac        1104
Pro Asn Phe Thr Thr Trp Ile Thr Tyr Gly Pro Asn Ile Thr Gly His
                355                 360                 365 cgc cgt agc agg cgc tcg ctg agt cgt ctc tca cct gac tgc ggt gat        1152
Arg Arg Ser Arg Arg Ser Leu Ser Arg Leu Ser Pro Asp Cys Gly Asp
            370                 375                 380 gag cta cag cta tgg agt gtg aca gcc cgg ata ttt gct tct ttc ttt        1200
Glu Leu Gln Leu Trp Ser Val Thr Ala Arg Ile Phe Ala Ser Phe Phe
        385                 390                 395 gct cct ggt gta gct gca caa gcc tta aag gag att gaa cgc ttg            1248
Ala Pro Gly Val Ala Ala Gln Ala Leu Lys Glu Ile Glu Arg Leu
    400                 405                 410 gca tgt tgg tcg gtt aag caa gcg aat tta aca tca tta ata ttg aat        1296
Ala Cys Trp Ser Val Lys Gln Ala Asn Leu Thr Ser Leu Ile Leu Asn
415                 420                 425                 430 gcg atg ctg gag gac atg aac agc atc cgg cac gcg gtg ttg cag aat        1344
Ala Met Leu Glu Asp Met Asn Ser Ile Arg His Ala Val Leu Gln Asn
                435                 440                 445 cga gca gcc atc gat ttc tta ctc ctg gcg caa gga cac ggg tgt caa        1392
Arg Ala Ala Ile Asp Phe Leu Leu Leu Ala Gln Gly His Gly Cys Gln
```

-continued

```
                   450                 455                 460
gac gtg gaa ggg atg tgt tgc ttc aat ctc agc gat cac agt gag tcc    1440
Asp Val Glu Gly Met Cys Cys Phe Asn Leu Ser Asp His Ser Glu Ser
            465                 470                 475 att cac aag gcg ctt caa gcc atg aag gaa cat aca gag aag ata cgg    1488
Ile His Lys Ala Leu Gln Ala Met Lys Glu His Thr Glu Lys Ile Arg
        480                 485                 490 gtg gaa gat gat ccc ata ggg gat tgg ttt acg cgc acg ttt ggt ggt    1536
Val Glu Asp Asp Pro Ile Gly Asp Trp Phe Thr Arg Thr Phe Gly Gly
495                 500                 505                 510 ctt gga ggg tgg ctc gca aaa ggc gtt aag acg cta ctg ttt gcc ttg    1584
Leu Gly Gly Trp Leu Ala Lys Gly Val Lys Thr Leu Leu Phe Ala Leu
                515                 520                 525 ctt gtc ata gtc tgt cta tta gct atc att cca tgt ata atc aag tgc    1632
Leu Val Ile Val Cys Leu Leu Ala Ile Ile Pro Cys Ile Ile Lys Cys
            530                 535                 540 ttc cag gat tgt cta tcg aga aca atg tat cag ctt atg gat gaa cgc    1680
Phe Gln Asp Cys Leu Ser Arg Thr Met Tyr Gln Leu Met Asp Glu Arg
        545                 550                 555 ata aga tat cat aga att agg gag cag ctg taggtcgac                   1719
Ile Arg Tyr His Arg Ile Arg Glu Gln Leu
        560                 565
```

<210> SEQ ID NO 2
<211> LENGTH: 568
<212> TYPE: PRT
<213> ORGANISM: Avian leukosis virus

<400> SEQUENCE: 2

```
Met Glu Ala Val Ile Lys Ala Phe Leu Thr Gly His Pro Gly Lys Val
 1               5                  10                  15

Ser Lys Lys Asp Ser Lys Lys Pro Pro Ala Thr Ser Lys Lys Asp
            20                  25                  30

Pro Glu Lys Thr Pro Leu Leu Pro Ser Arg Gly Tyr Phe Phe Gln
        35                  40                  45

Met Ile Leu Val Cys Val Val Ile Ile Ser Val Val Pro Gly Val Gly
    50                  55                  60

Gly Val His Leu Leu Gln Gln Pro Gly Asn Val Trp Val Thr Trp Ala
65                  70                  75                  80

Asn Lys Thr Gly Arg Thr Asp Phe Cys Leu Ser Leu Gln Ser Ala Thr
                85                  90                  95

Ser Pro Phe Arg Thr Cys Leu Ile Gly Ile Pro Gln Tyr Pro Leu Ser
            100                 105                 110

Thr Phe Glu Gly Tyr Val Thr Asn Val Thr Ala Cys Asp Asn Ser Ala
        115                 120                 125

Asp Leu Ala Asn Gln Thr Ala Cys Leu Ile Lys Ala Leu Asn Thr Thr
    130                 135                 140

Leu Pro Trp Asp Pro Gln Glu Leu Asp Ile Leu Gly Ser Gln Met Ile
145                 150                 155                 160

Lys Asn Gly Thr Lys Arg Thr Cys Val Thr Phe Gly Ser Val Cys Tyr
                165                 170                 175

Lys Glu Asp Asn Ser Thr Val Cys His Asn Phe Asp Gly Asn Phe Asn
            180                 185                 190

Gly Thr Gly Gly Ala Glu Ala Glu Leu Arg Asp Phe Ile Ala Lys Trp
        195                 200                 205

Lys Ser Asp Asp Pro Leu Ile Arg Pro Tyr Val Asn Gln Ser Trp Thr
    210                 215                 220
```

```
Met Val Ser Pro Ile Asn Thr Glu Ser Phe Ser Ile Ser Ser Arg Tyr
225                 230                 235                 240

Cys Gly Phe Thr Ser Asn Glu Thr Arg Tyr Tyr Arg Gly Asn Phe Ser
                245                 250                 255

Asn Trp Cys Gly Ser Lys Gly Gly Lys Trp Ser Ala Gly Tyr Ser Asn
                260                 265                 270

Gly Thr Glu Cys Ser Asp Gly Thr Ala Gly Cys Gly Asn Cys Thr
            275                 280                 285

Ala Glu Trp Asn Tyr Tyr Ala Tyr Gly Phe Thr Phe Gly Asn Lys Pro
290                 295                 300

Glu Ile Leu Trp Asn Asn Gly Thr Ala Lys Ala Leu Pro Pro Gly Ile
305                 310                 315                 320

Phe Leu Ile Cys Gly Asp Arg Ala Trp Gln Gly Ile Pro Ser Asn Ala
                325                 330                 335

Leu Gly Gly Pro Cys Tyr Leu Gly Gln Leu Thr Met Leu Ser Pro Asn
                340                 345                 350

Phe Thr Thr Trp Ile Thr Tyr Gly Pro Asn Ile Thr Gly His Arg Arg
                355                 360                 365

Ser Arg Arg Ser Leu Ser Arg Leu Ser Pro Asp Cys Gly Asp Glu Leu
370                 375                 380

Gln Leu Trp Ser Val Thr Ala Arg Ile Phe Ala Ser Phe Ala Pro
385                 390                 395                 400

Gly Val Ala Ala Ala Gln Ala Leu Lys Glu Ile Glu Arg Leu Ala Cys
                405                 410                 415

Trp Ser Val Lys Gln Ala Asn Leu Thr Ser Leu Ile Leu Asn Ala Met
                420                 425                 430

Leu Glu Asp Met Asn Ser Ile Arg His Ala Val Leu Gln Asn Arg Ala
            435                 440                 445

Ala Ile Asp Phe Leu Leu Leu Ala Gln Gly His Gly Cys Gln Asp Val
450                 455                 460

Glu Gly Met Cys Cys Phe Asn Leu Ser Asp His Ser Glu Ser Ile His
465                 470                 475                 480

Lys Ala Leu Gln Ala Met Lys Glu His Thr Glu Lys Ile Arg Val Glu
                485                 490                 495

Asp Asp Pro Ile Gly Asp Trp Phe Thr Arg Thr Phe Gly Gly Leu Gly
                500                 505                 510

Gly Trp Leu Ala Lys Gly Val Lys Thr Leu Leu Phe Ala Leu Leu Val
                515                 520                 525

Ile Val Cys Leu Leu Ala Ile Ile Pro Cys Ile Ile Lys Cys Phe Gln
            530                 535                 540

Asp Cys Leu Ser Arg Thr Met Tyr Gln Leu Met Asp Glu Arg Ile Arg
545                 550                 555                 560

Tyr His Arg Ile Arg Glu Gln Leu
                565

<210> SEQ ID NO 3
<211> LENGTH: 41
<212> TYPE: DNA
<213> ORGANISM: Avian leukosis virus

<400> SEQUENCE: 3
ggggatccat ggaagccgtc ataaaggcat ttctgactgg g          41

<210> SEQ ID NO 4
```

```
<211> LENGTH: 27
<212> TYPE: DNA
<213> ORGANISM: Avian leukosis virus

<400> SEQUENCE: 4
ggggtcgacc tacagctgct ccctaat                                       27

<210> SEQ ID NO 5
<211> LENGTH: 24
<212> TYPE: DNA
<213> ORGANISM: Avian leukosis virus

<400> SEQUENCE: 5
tttactgttt tcgtaacagt tttg                                          24

<210> SEQ ID NO 6
<211> LENGTH: 21
<212> TYPE: DNA
<213> ORGANISM: Avian leukosis virus

<400> SEQUENCE: 6
caacaacgca cagaatctag c                                             21
```

AVIAN LEUKOSIS VIRUS SUBGROUP J ENVELOPE GENE PRODUCT FOR DIAGNOSIS AND IMMUNOGENIC COMPOSITION

This application claims the benefit under 35 U.S.C. §119(e) of U.S. provisional application Ser. No. 60/093,632, filed on Jul. 21, 1998.

BACKGROUND OF THE INVENTION

1. Field of the Invention

The present invention relates to avian leukosis virus (ALV) subgroup J strain Hc1 envelope (env) gene and gene products for use in diagnosis and vaccine development.

2. Description of Related Art

Avian leukosis virus (ALV) is the most common naturally occurring avian retrovirus associated with neoplastic diseases and other production problems in chickens [Crittenden, *Avian Pathol.*, 10:101–112 (1981); Payne and Fadley, *Diseases of Poultry*, 10th Ed., 414–466, (1997)]. It comprises eight subgroups based on envelope properties. This group of viruses is capable of inducing a variety of neoplasms, but lymphoid leukosis is the most common naturally occurring B-cell lymphoma of chickens. A newly emerged subgroup J (ALV-J) was first isolated in England in 1989 and in the United States in 1994. Infections caused by this virus reached epidemic proportions in 1996. The total loss in commercial broiler breeders is currently estimated to be 1.5% per week in excess of normal mortality and represents a major economic loss for the poultry industry. In view of these astounding numbers collected over the past five years, the newly emerging ALV-J has been elevated to the top of the disease priority list for the poultry broiler breeder industry.

ALV-J was first reported in the United Kingdom in 1991 and was found to be associated with myeloid leukosis (ML) in meat-type chickens [Payne et al., *J. Gen. Virol.*, 72:801–807 (1991); Payne et al., *Vet. Record*, 129:447–448 (1991), Payne et al., *Leukemia*, 6:1167–1176, (1992); Payne et al., *Avian Dis.*, 37:438–450, (1993)]. ALV Strain HPRS-103, the prototype of ALV-J appears to be a recombinant between ALV and ancient endogenous avian retroviral envelope (E51) sequences [Bai et al., *J. Gen. Virol.*, 76:181–187 (1995); Bai et al., *J. Virol.*, 69:779–784 (1995)]. Because ML was induced experimentally only after a long latent period, it has been proposed that strain HPRS-103 of ALV-J does not contain an oncogene and was therefore more closely related to other slowly transforming strains of ALV [Payne and Fadley, *Diseases of Poultry*, 10th Ed., 414–466, (1997)]. However, acutely transforming ALVs were recovered from ML induced experimentally by HPRS-103 [Payne et al., *Avian Dis.*, 37:438–450 (1993)].

The sequence of the complete proviral genome was reported to be a multiple recombinant of at least five ALV sequences and one endogenous avian retroviral (EAV) sequence [Bai et al., *J. Gen. Virol.*, 76:181–187 (1995); Bai et al., *J. Virol.*, 69:779–784, (1995)]. The HPRS-103 env is reported to be closely related to the env gene of the defective EAV-E51 but divergent from those of other ALV subgroups [Bai et al., *J. Gen. Virol.*, 76:181–187 (1995); Bai et al., *J. Virol.*, 69:779–784, (1995)]. The nucleotide sequence of the env gene of HPRS-103 was shown to have 40% identity with the corresponding regions of the other ALV subgroups [Bai et al., *J. Gen. Virol.*, 76:181–187 (1995); Bai et al., *J. Virol.*, 69:779–784, (1995)].

Venugopal et al. [*Avian Dis.*, 41:283–288 (1997)] described the construction of a recombinant baculovirus containing the cloned DNA encoding the gp85 envelope glycoprotein of HRPS-103. They fused the env DNA to the carboxy-terminus of the affinity tag glutathione-S-transferase. Their fusion protein was secreted into the supernatant medium of the infected insect cell culture. Using the recombinant protein in ELISA assay, they found the assay to be specific and sensitive for detection of HRPS-103 virus-specific antibodies in the sera of infected birds.

SUMMARY OF THE INVENTION

We have now isolated and sequenced the envelope (env) gene from Hc1 strain of ALV-J virus and have cloned the gene into an expression vector. The ALV-J Hc1 env gene and expressed protein are useful for development of diagnostic assays to detect ALV-J Hc1-specific nucleic acid and proteins in chickens and for the development of an ALV vaccine.

In accordance with this discovery, it is an object of the invention to provide unique isolated and sequenced env gene from the Hc1 strain of ALV-J.

It is also an object of the invention to clone the ALV-J Hc1 env gene into an expression vector for generation of the envelope protein.

Another object of the invention is to provide antibody to ALV-J Hc1 env antigen, wherein the antibody neutralizes both ALV-J Hc1 and ALV-J HPRS-103.

A further object of the invention is to provide reagents for use in a diagnostic kit for assaying for ALV-J in poultry flocks.

Still another object of the invention is to provide a subunit vaccine for eliciting an immunune response to ALV-J in poultry.

Other objects and advantages of the invention will become readily apparent from the ensuing description.

BRIEF DESCRIPTION OF THE DRAWINGS

Figure 4A:
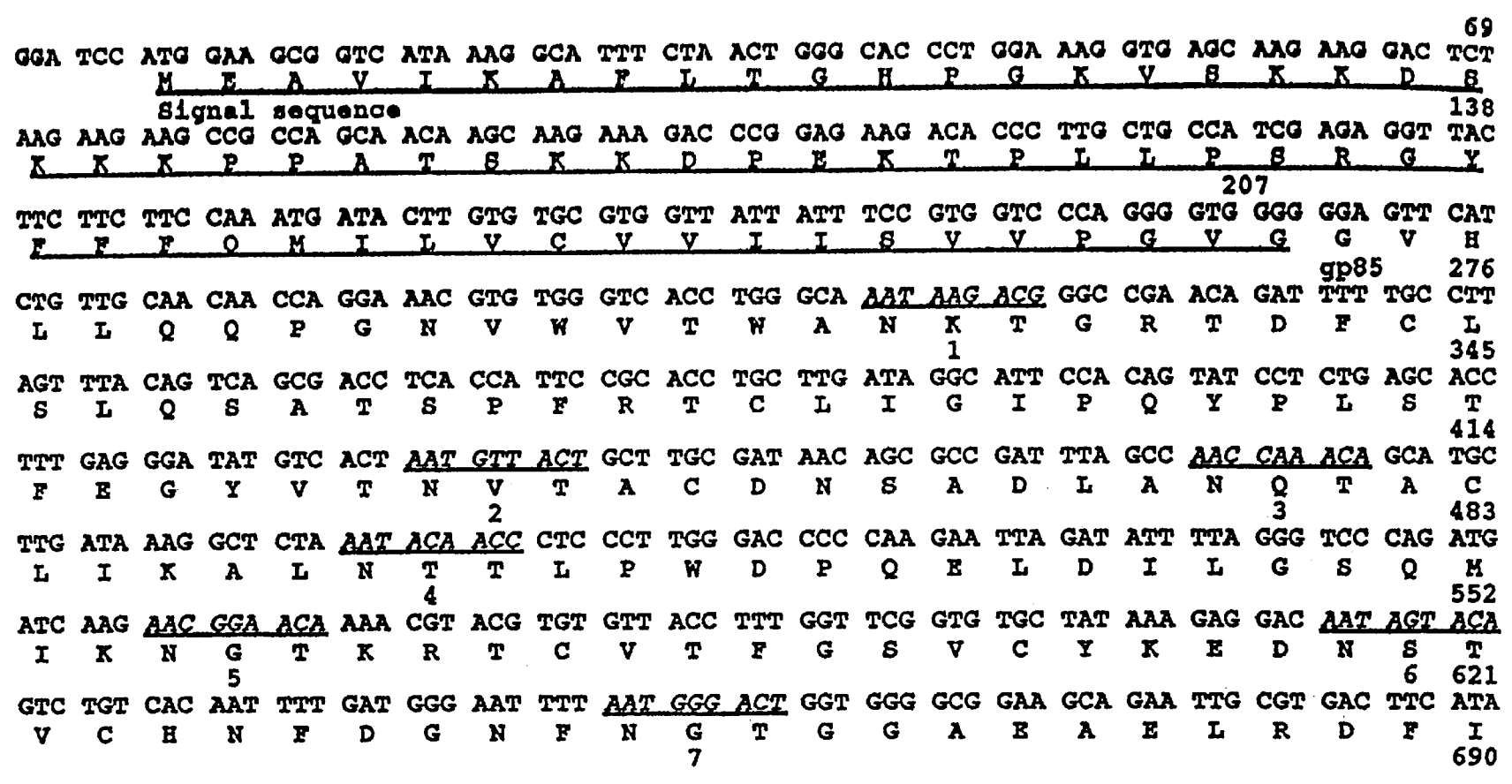

FIGS. 4A–4C shows the nucleotide and amino acid sequences corresponding to the ADOL-Hc1 env gene. The signal sequence and gp37 region are underlined and labeled, and the gp85 region is also indicated. There are 17 potential N-linked glycosylation sites, which are indicated in underlined italics and numbered. Fifteen of these sites are located within gp85, and 2 are located in gp37.

DEFINITIONS

Figure 1:
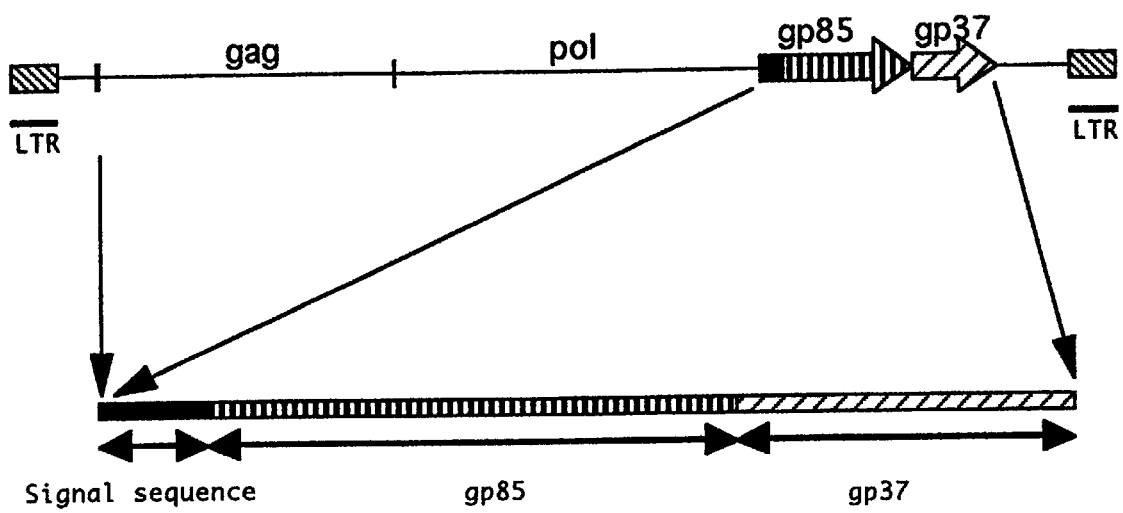
FIG. 1 is a putative genomic map for ALV-J Hc1.

The following terms are used herein:

Cloning: The selection and propagation of (a) genetic material from a single individual, (b) a vector containing one gene or gene fragment, or (c) a single organism containing one such gene or gene fragment.

Cloning Vector: A plasmid, virus, retrovirus, bacteriophage or nucleic acid sequence which is able to replicate in a host cell, characterized by one or a small number of restriction endonuclease recognition sites at which the sequence may be cut in a predetermined fashion, and which contains a marker suitable for use in the identification of transformed cells, e.g., tetracycline resistance or ampicillin resistance. A cloning vector may or may not possess the features necessary for it to operate as an expression vector.

DNA Coding Sequence: A DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxy) terminus. In the case of retroviruses, the coding sequence can include, but is not limited to, the genomic RNA as well as the cDNA and proviral DNA. A polyadenylation signal and transcription termination sequence will usually be located 3' to the coding sequence.

Expression: The process undergone by a structural gene to produce a polypeptide. Expression requires both transcription of DNA and translation of RNA.

Expression Vector: A replicon such as a plasmid, virus, retrovirus, bacteriophage, or nucleic acid sequence which is able to replicate in a host cell, characterized by a restriction endonuclease recognition site at which the sequence may be cut in a predetermined fashion for the insertion of a heterologous DNA sequence. An expression vector has a promoter positioned upstream of the site at which the sequence is cut for the insertion of the heterologous DNA sequence, the recognition site being selected so that the promoter will be operatively associated with the heterologous DNA sequence. A heterologous DNA sequence is "operatively associated" with the promoter in a cell when RNA polymerase which binds the promoter sequence transcribes the coding sequence into mRNA which is then in turn translated into the protein encoded by the coding sequence.

Fusion Protein: A protein produced when two heterologous genes or fragments thereof coding for two different proteins not found fused together in nature are fused together in an expression vector. For the fusion protein to correspond to the separate proteins, the separate DNA sequences must be fused together in correct translational reading frame.

Gene: A segment of DNA which encodes a specific protein or polypeptide, or RNA.

Genome: The entire genetic complement of an organism. It includes, among other things, the structural genes encoding for the polypeptides of the substance, as well as operator, promoter and ribosome binding and interaction sequences. In the case of retroviruses, the genome is RNA.

Heterologous DNA: A DNA sequence inserted within or connected to another DNA sequence which codes for polypeptides not coded for in nature by the DNA sequence to which it is joined. Allelic variations or naturally occurring mutational events do not give rise to a heterologous DNA sequence as defined herein.

Hybridization: The pairing together or annealing of single stranded regions of nucleic acids to form double-stranded molecules.

Plasmid: A non-chromosomal double-stranded DNA sequence comprising an intact "replicon" such that the plasmid is replicated in a host cell. When the plasmid is placed within a unicellular organism, the characteristics of that organism may be changed or transformed as a result of the DNA of the plasmid. A cell transformed by a plasmid is called a "transformant."

Promoter: A DNA sequence within a larger DNA sequence defining a site to which RNA polymerase may bind and initiate transcription.

Recombinant DNA Molecule: A hybrid DNA sequence comprising at least two DNA sequences, the first sequence not normally being found together in nature with the second.

Replicon: Any genetic element (e.g., plasmid, chromosome, virus) that functions as an autonomous unit of DNA replication in vivo, i.e., capable of replication under its own control.

Structural Gene: A DNA sequence which encodes through its template or messenger RNA (mRNA) a sequence of amino acids characteristic of a specific polypeptide or protein.

Transform: To change in a heritable manner the characteristics of a host cell in response to DNA foreign to that cell.

Transcription: The process of producing mRNA from a structural gene.

Translation: The process of producing a polypeptide from mRNA.

DETAILED DESCRIPTION OF THE INVENTION

ALV genomic structure is composed of a dimeric single stranded RNA genome enclosed in a core of viral protein which is wrapped with a glycoprotein envelope. The genome is composed of three major genes, gag, pol and env flanked by the LTRs. Env is a fragment of about 1.7 kb and encodes two glycoproteins, gp85 and gp37 (FIG. 1).

The ALV-J HC1 env gene for use in this invention was isolated by polymerase chain reaction from Hc1 proviral DNA as discussed further, below.

The present invention provides an isolated nucleic acid molecule comprising the env gene (SEQ ID NO:1) of ALV-J, strain Hc1. The nucleic acid may be, without limitation thereto, the original genomic RNA, cDNA reverse transcribed from the genomic RNA, a fragment of host cell DNA comprising such cDNA as proviral DNA, or a construct comprising any such RNA or DNA, in single or double stranded form, as heterologous nucleic acid. Also encompassed are variations of the env gene which encode the env protein or functional equivalents of the protein. Functional equivalents of the ALV-J, strain Hc1 env protein are considered herein to be any variations which share the same neutralization epitope with the Hc1 env protein such that antibody elicited to the protein neutralizes both strains HPRS-103 and ADOL-Hc1 of ALV-J as discussed further below.

Because of the degeneracy of the genetic code, there exists a finite set of nucleotide sequences which can code for a given amino acid sequence. It is understood that all such equivalent sequences are operable variants of the disclosed sequence, since all encode the same protein (i.e., the same amino acid sequence) during in vivo transcription and translation, and are hence encompassed by the instant invention. Nucleic acid sequences which are substantially homologous to the nucleotide sequence of SEQ ID NO:1 are also encompassed by the invention. As defined herein, two DNA sequences are substantially homologous when they share at least 95% (preferably at least 98%) sequence identity with SEQ ID NO:1.

It is envisioned that the ALV-J Hc1 env gene will be useful for detecting proviral DNA or genomic RNA of the ALV-J virus in blood or other tissue samples upon amplification by PCR or the like. The env gene may also be useful for in vivo expression of the env protein.

The invention also provides the ALV-J strain Hc1 env protein (SEQ ID NO:2), as well as functional equivalents thereof as defined above, and also fusion proteins. The practitioner of ordinary skill in the art will recognize that slight deviations of the amino acid sequences may be made without affecting the immunogenicity of the protein. Substantial equivalents of the above protein include conservative substitutions of amino acids with other amino acids, including either naturally occurring or non-conventional amino acids, which maintain substantially the same charge and hydrophobicity as the original amino acid. Conservative substitutions include for example, replacement of glycine for alanine, valine for isoleucine, leucine for isoleucine, aspartic acid for glutamic acid, lysine for arginine, asparagine for glutamine, phenylalanine for tryptophan, and tryptophan for tyrosine. Examples of conservative substitutions with non-conventional amino acids are described in Rosenberg et al. (U.S. Pat. No. 5,679,782) the contents of which are incorporated by reference herein.

The env protein of the invention is characterized by a calculated molecular weight of 63 kD based on the amino acid sequence. However, the observed molecular weight may be higher. For example, when immunoprecipitation of 35S methionine-labeled cell proteins is carried out with polyclonal chicken serum, a protein band with a Mw about 90 kD is detected in infected cells. This difference in molecular weight is expected because of the large numbers of potential N-glycosylation sites (17 sites) throughout the env protein. It is envisioned that the ALV-J Hc1 env protein encoded by the env gene will be useful as a reagent probe for detecting antibodies to subgroup J viruses, as an agent for interfering with virus replication, and as a subunit vaccine against the disease. This reagent probe will be highly sensitive and specific for only ALV-J virus infection and will identify active ALV-J infection in chickens.

For applications requiring administration to an animal, the env protein may be formulated with a compatible, physiologically acceptable diluent or carrier such as phosphate buffered saline. The proteins may be administered to a target animal by any convenient route, including intramuscularly, intraperitonealy or preferably subcutaneously, in a single dose or in a plurality of doses. The protein may also be administered in combination with optional stabilizers and immunopotentiating agents or adjuvants. Typical stabilizers include, for example, sucrose, an alkali metal hydrogen phosphate salt, glutamate, serum albumin, gelatin, or casein. A variety of adjuvants are suitable for use herein, although a mixture of alhydrogel and amphigen is preferred. Other conventional adjuvants which may be suitable for use herein include those described by Davis et al. (ed.) (Microbiology, second edition, Harper & Row, Hagerstown, Md., 1973, pp. 480–482), the contents of which are incorporated by reference herein.

The concentration and amount of the protein in the final composition may vary depending upon the desired use and type of response needed, and on the host animal. In any event, the protein should be employed in an amount effective to induce the preferred response as determined by routine testing. Generally, the proteins are administered to the target animal in an amount effective to elicit an immune response in a subject animal as compared to an untreated control. The effective amount will vary with the particular target animal, its age and size, and may be readily determined by the practitioner skilled in the art. Typically, a vaccine would be administered by subcutaneous or intramuscular injection.

One objective of antibody production is for use in the development of a diagnostic assay or assay kit for detecting the presence of ALV-J in poultry. A variety of conventional immunoassay techniques are suitable for use herein, including RIA, or ELISA, or double antibody sandwich immunoassays. It is envisioned that the antibody would also be useful as a vaccine for the passive immunization of poultry against ALV-J. The fact that antibody to ADOL-Hc1 neutralized HPRS-103 virus, whereas antibody to HPRS-103 did not neutralize ADOL-Hc1 virus suggests that both strains are antigenically related, but not identical. This one-way neutralization suggested that ADOL-Hc1 has a unique neutralization epitope and is more likely to cross react with future ALV-J isolates.

In an alternative embodiment, the protein may be used as an immunodiagnostic reagent for binding and detecting antibodies in the serum of an animal. Detection of antibodies against ALV-J in the sera of animals may be used for monitoring and detecting animals which are carriers of the virus but which do not show outward signs of infestation, as well as identifying animals previously exposed or infected with ALV-J. Again, a variety of conventional immunoassays are suitable for use herein, although ELISA is preferred. For example, in an ELISA test the purified protein of this invention may be used as an antigen bound to the wells of a microtiter plate. Following contact of the test animal sera with the adsorbed antigen, bound anti-ALV-J antibodies may then be detected.

The DNA sequences of the invention can be used to prepare recombinant DNA molecules by cloning in any suitable vector. A variety of vector-host cell expression systems may be employed in practicing the present invention. Host cells of particular interest are chicken embryo fibroblasts (CEF), though selection of other suitable host cells could be determined by the skilled artisan.

Vectors used in practicing the present invention are selected to be operable as cloning vectors or expression vectors in the selected host cell. Numerous vectors are readily available, and selection of an appropriate vector and host cell is a matter of choice. The vectors may, for example, be bacteriophage, plasmids, viruses, or hybrids thereof. In the preferred practice of the invention, the desired nucleic acid fragment is cloned into a baculovirus or a fowlpox virus transfer vector such as pBlueBac2A or pBlueBac4.

Within each specific vector, various sites may be selected for insertion of the isolated DNA sequence. These sites are usually designated by the restriction enzyme or endonuclease that cuts them. For example, in pBlueBac2A or pBlueBac4, the BamHI and the SalI sites are typically used.

The DNA sequences of the invention may be inserted into the desired vector by known techniques. If, however, the vector is to serve as an expression vector, it should have a promoter, and the DNA sequence should be inserted in the vector downstream of the promoter and operationally associated therewith. While control sequences may be ligated to the coding sequence prior to insertion into the vector, preferably, the vector should be selected so as to have a promoter operable in the host cell into which the vector is to be inserted (that is, the promoter should be recognized by the RNA polymerase of the host cell).

In general, after construction of a suitable expression system, the system is transfected into the appropriate host and successful transformants may be selected by markers contained on the expression vectors. Successfully transformed colonies are then cultured for abundant expression of the protein. The recombinant protein may then be recovered from the medium or from the cells using suitable techniques generally known in the art, and purified by, for example, ion exchange chromatography, ammonium sulfate precipitation, or gel permeation chromatography.

The following examples are intended only to further illustrate the invention and are not intended to limit the scope of the invention which is defined by the claims.

EXAMPLE 1

Location and isolation of Hc1 env gene from Hc1-infected cells.

The ADOL-Hc1 isolate was obtained from C/AE CEF inoculated with peripheral blood monocytes (PBM) from an affected GGP flock was biologically cloned by terminal dilution and was considered to be the prototype of the ALV-J isolated in the United States. CEF were grown in Leibowitz-McCoy medium (GIBCO Laboratories), supplemented with 4% calf serum (growth medium) or 1% calf serum (maintenance medium). Line 0 chicken embryo fibroblasts were infected with $10^4$ infectious units of Hc1 virus per $10^7$ cells. After 7 days post-infection, total DNA was extracted according to standard procedure and used as template for env gene isolation by polymerase chain reaction (PCR).

Figure 2:
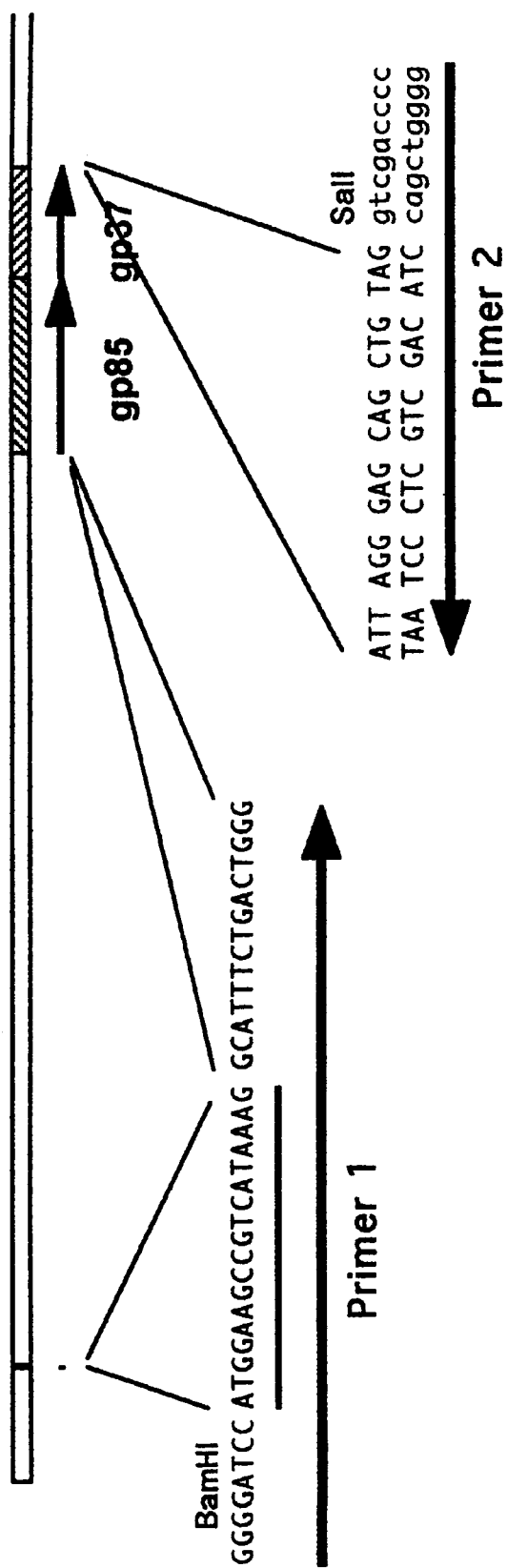
FIG. 2 shows primers used for amplification of the env gene of ALV-J Hc1 by PCR.

Based on the published sequences from HPRS-103, two primers were designed: 5'-GGGGATCCATGGAAGC-CGTCATAAAGGCATTTCTGACTGGG (forward primer; SEQ ID NO:3) and 3'-GGGGTCGACCTACAGCTGCTCCCTAAT (reverse primer; SEQ ID NO:4). These two primers expanded a 1.7 kb fragment of the ADOL-Hc1 proviral DNA that encompasses gp85 and gp37 (FIG. 2). The 5'end of the forward primer contains a BamHI site and 18 bp signal sequences. The 3'end of reverse primer 2 contains a SalI site. These two sites were created for cloning convenience into baculovirus or fowlpox viruses.

Figure 3:
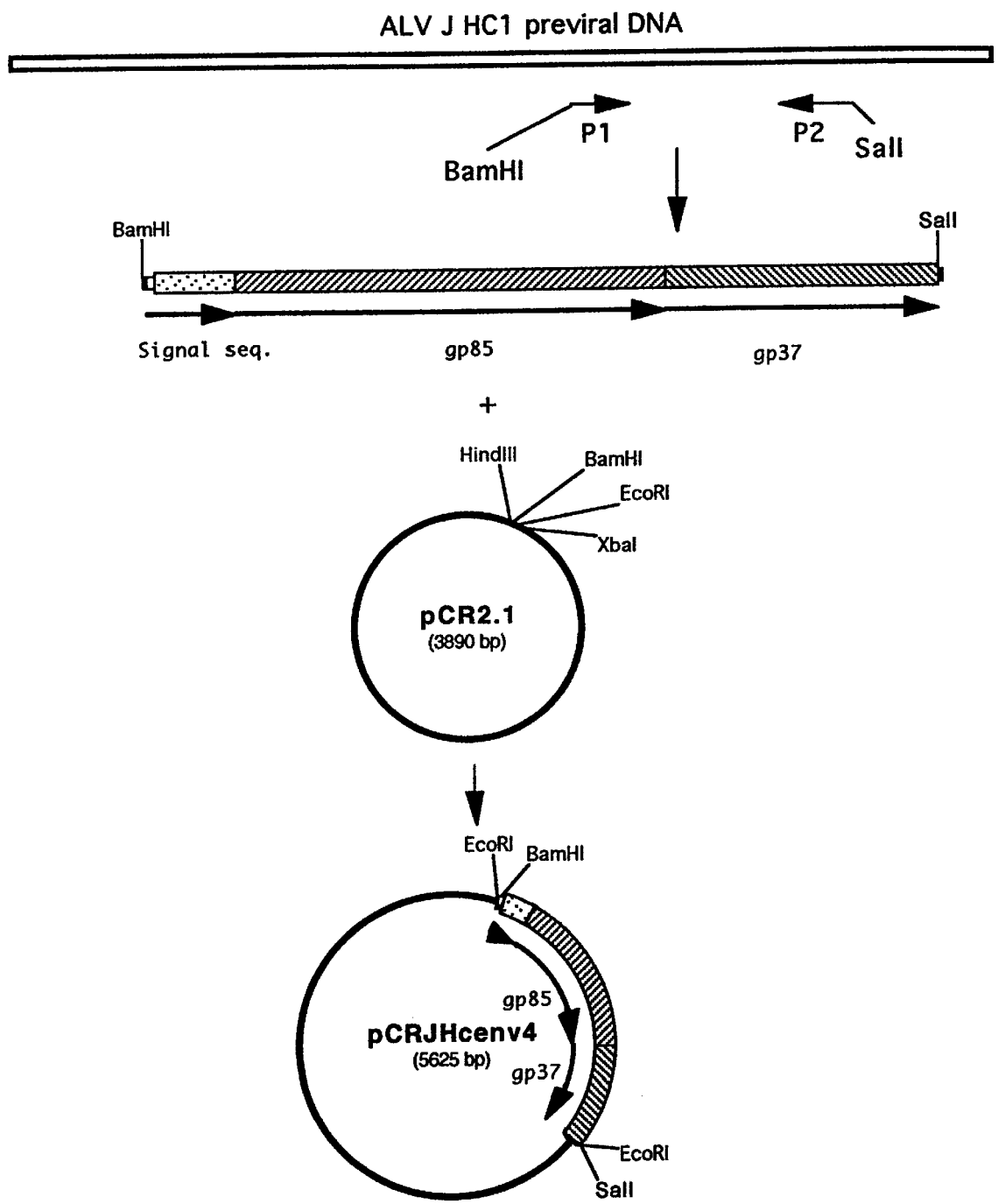
FIG. 3 shows construction of the pCRJHcenv4 plasmid clone from the PCR amplification products of env gene and the pCR 2.1 cloning vector.
Figure 5:
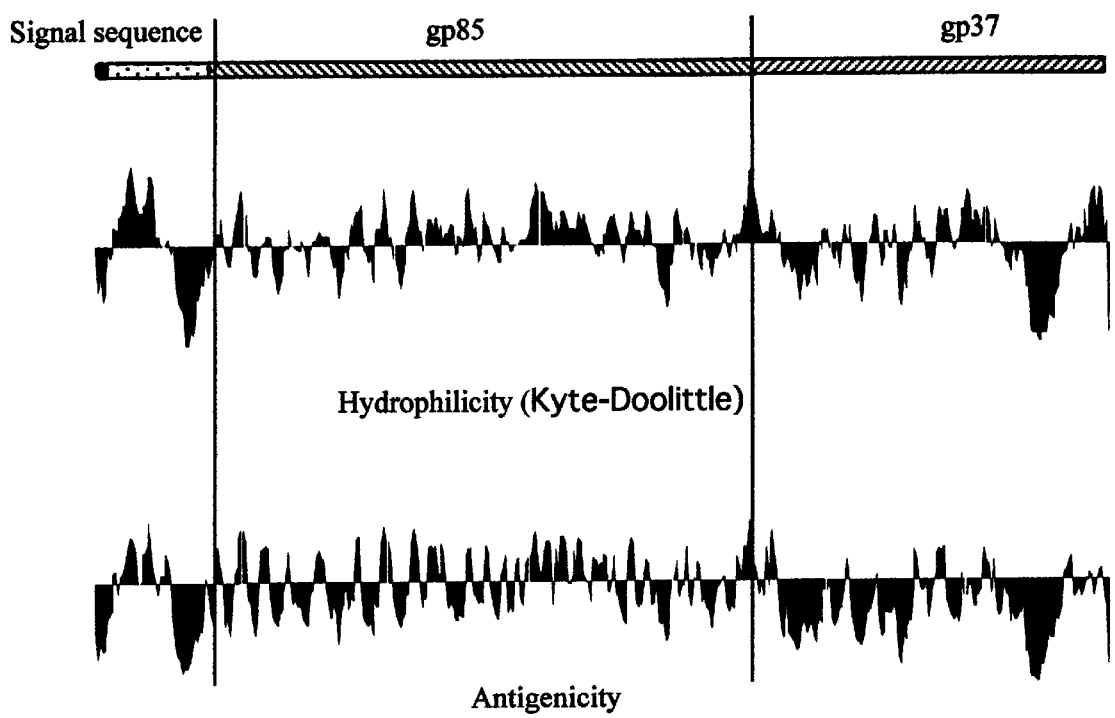
FIG. 5 depicts the hydrophilicity and antigenicity profiles of ALV-J HC1 env gene.
Figure 6:
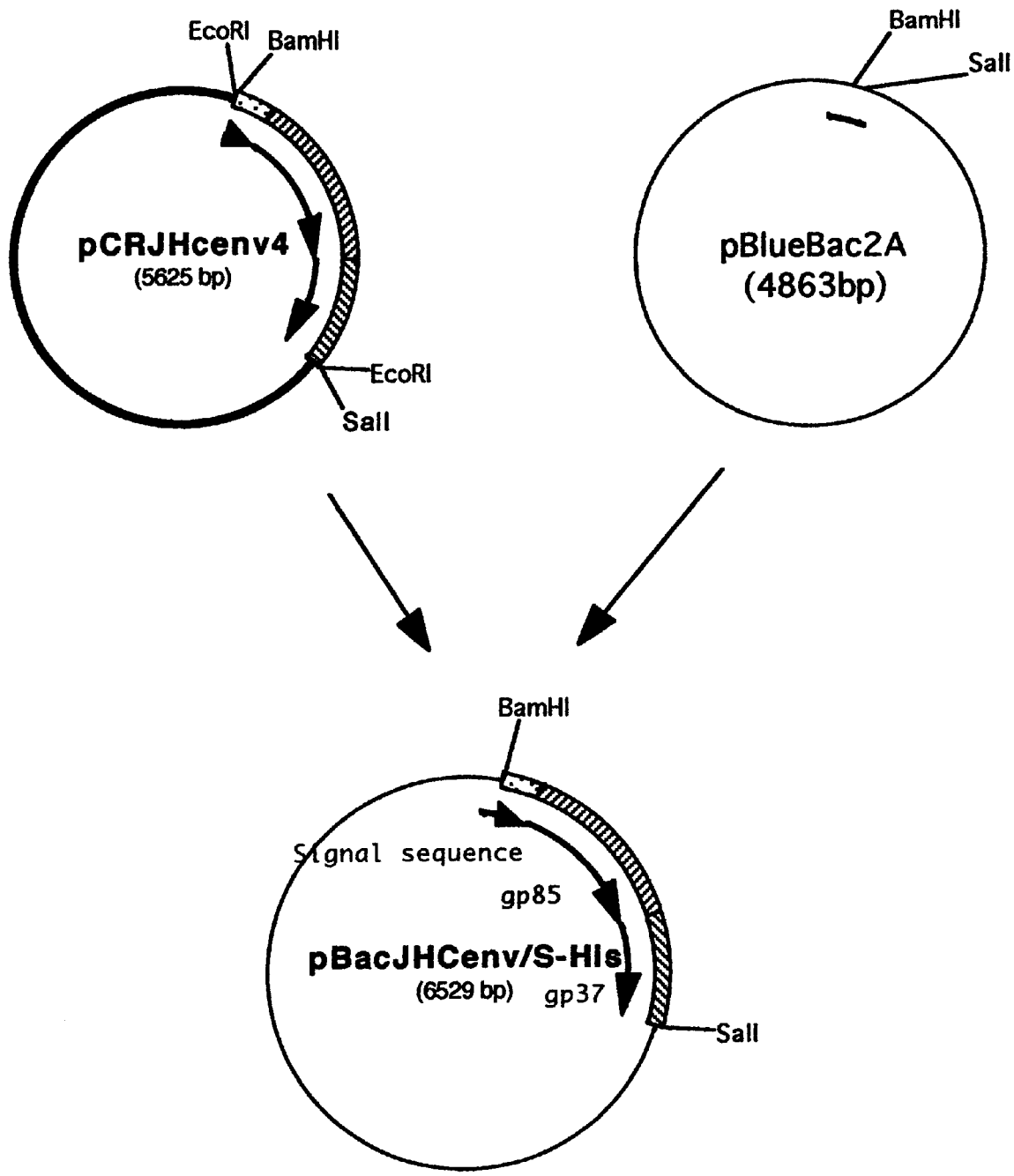
FIG. 6 shows the construction of pBacJHCenv/S-His transfer vector containing the Hc1 env gene insert. This vector is used to generate recombinant baculovirus reBacJHCenv/S-His.
Figure 7:
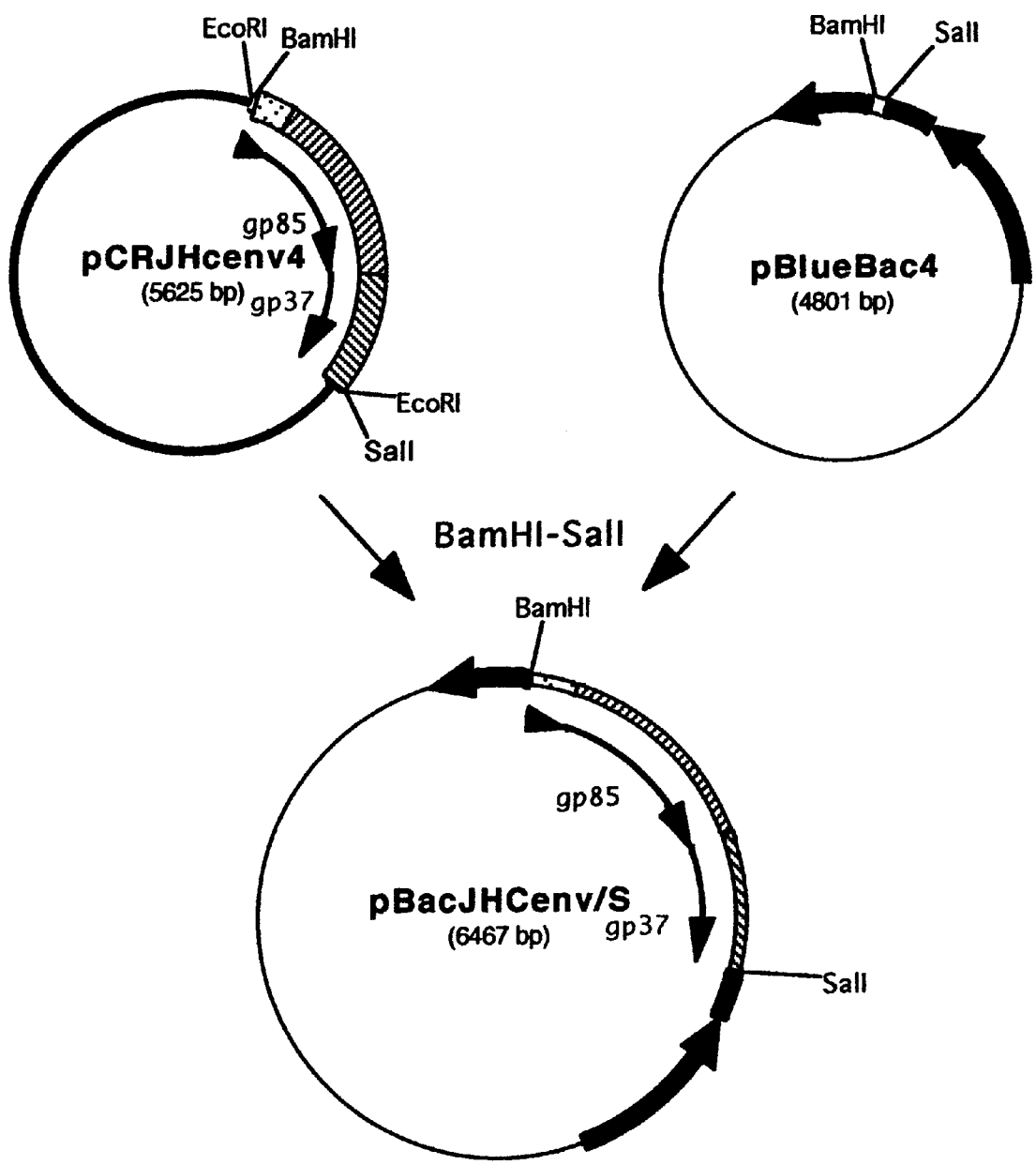
FIG. 7 shows the construction of pBacJHCenv/S transfer vector containing the Hc1 env gene insert. This vector is used to generate recombinant baculovirus reBacJHCenv/S.

The PCR reaction was carried out according to the method of Smith et al. [Avian Dis., 42:375–380, (1998)], as follows: 25 µl PCR reaction mixture was setup with 2.5 µl DNA (10–100 ng/ml), 2.5 ml 10× PCR buffer, 2 µl 25 mM $Mg^{++}$, 1 µl 25 mM dNTPs, 1 µl PCR primer mixture (5 picomol/each), 0.5 µl (1 nit) Taq polymerase, sterile water to 25 ml. The mixture was overlaid with 30 µl mineral oil. PCR reaction was executed in MiniCycler (M J Research Inc., Watertown, Mass.) with the following parameters: step 1, initial denaturation at 94° C. for 2 minutes; step 2, denaturation at 94° C. for 1 minute; step 3, annealing at 59° C. for 2 minutes; step 4, extension at 72° C. for 3 minutes; step 5, 30 cycles between step 2 and 4; step 6, final extension at 72° C. for 7 minutes; and step 7, holding the reaction at 15° C. until analyzed in 1% agarose gel electrophoreses. The PCR amplifed product was cloned into pCRII TA cloning vector (Invitrogen). This resulted in a plasmid clone with the entire Hc1 envelope gene encoding gp85 and gp37 and was designated as pCRJHcenv4 (FIG. 3).

EXAMPLE 2

Biological Cloning.

The ADOL-Hc1 strain of ALV-J virus isolated from Example 1 was biologically cloned. Peripheral blood monocytes or plasma from chickens inoculated with ADOL-Hc1 virus were used to infect C/E (resistant to infection with endogenous ALV) line 0 CEF and C/AE (resistant to infection with subgroup A and E ALV) alv6 CEF; 7 to 9 days later, cell lysates were tested for the presence of ALV group-specific antigen by an ELISA as described [Smith et al., Avian Dis., 23:698–707, (1979)]. Antigenic relationship of the initial isolate (ADOL-Hc1) to other groups of ALV was determined by cross neutralization tests as described [Fadly, A. M. and Witter, R. L., In:*A Lab. Manual for the Isolation and Identification of Avian Pathogens,* J. R. Glisson, et al., (Eds), 4th Ed., Kennett Square, Am. Assoc. Avian Pathologists, (1998)]. The Hc1 virus thus obtained was considered biologically cloned.

EXAMPLE 3

DNA Sequencing and Analysis of ADOL-Hc1 env gene.

DNA sequencing was conducted with pCRJHCenv4 DNA (See Example 1) on an ABI360 automatic DNA sequencer. The initial sequence was obtained by using sequences from both ends of the PCR plasmid which include T7 forward and reverse primers. After obtaining sequences from both ends, primers based on these sequences were designed to enable walking through the entire env gene in both strands of DNA. The forward primer was 5'-TTT ACT GTT TTC GTA ACA GTT TTG-3' (SEQ ID NO:5) and the reverse primer was 5'-CAA CAA CGC ACA GAA TCT AGC-3' (SEQ ID NO:6). The open reading frames (ORF) searches, deduced amino acid sequence and plots were performed using Mac Vector (International Biotechnologies). The homology, alignment of amino acid sequences and calculation of pairwise percentage identities and similarities were performed by the Pileup, FastA and GAP program of the University of Wisconsin Genetics Computer Group (GCG) [Devereux et al., *Nucleic Acids Res.,* 12:387–395, (1984)]. The sequence of the 1.7 kb Hc1 env gene is shown in FIGS. 4A–4C.

Sequence analysis of the cloned PCR products from Hc1 env revealed that this strain is very closely related to HPRS-103, having a nucleotide sequence identity of 94%. Base differences in the respective genes were scattered throughout the genome.

EXAMPLE 4

Analysis of deduced amino acid sequence of ADOL-Hc1 env protein.

The amino acid sequence (SEQ ID NO:2) for the ADOL-Hc1 env gene is shown in FIGS. 4A–4C, and antigenicity and hydropholicity profiles are shown in FIG. 5. Cysteine residues, which are believed to maintain the overall secondary structure of the gp85 protein, were conserved between Hc1 and HPRS-103. A total of 14 potential glycosylation sites are found in gp85 and 2 in gp37. A $17^{th}$ site exists close to the carboxy-terminus of gp37, but since this is part of the intracytoplasmic tail of the polypeptide, it would not be expected to have carbohydrate added to it.

EXAMPLE 5

Comparison of ADOL-Hc1 to HPRS-103 envelopes.

The translated amino acid sequence of the ADOL-Hc1 envelope was aligned with the corresponding HPRS-103 sequence using the Pileup program of GCG. The identity score is approximately 94%. There is 90% overall similarity between the ADOL-Hc1 and HPRS-103 envelopes. The amino acid substitutions between ADOL-Hc1 and HPRS-103 appear more randomly distributed. The ADOL-Hc1 polymorphic substitutions disrupt two potential N-linked glycosylation sites in HPRS-103 but create two new sites at adjacent locations. The remaining 11 potential N-linked glycosylation sites in the SU domain are conserved between the two J viruses.

EXAMPLE 6

Cloning ALV-J Hc1 env gene into a Baculovirus Expression Vector.

The env gene was cloned into baculovirus in order to obtain abundant expression of the env protein. A fragment containing the env gene was cleaved from pCRJHcenv4 with BamHI and SalI, then cloned into pBlueBac 2A to generate pBacJHcenv/S-His transfer vector, which resulted in env protein with a His-tag (FIG. 6). Alternatively, the env gene-containing fragment was cloned into pBlueBac4 to generate pBacJHcenv/S, which resulted in an entire env protein without a His-tag (FIG. 7).

The procedure for developing recombinant viruses was as follows: $2\times10^6$ log phase Sf9 cells (98% viability) were seeded into a 60 mm tissue culture dish in 2 ml complete TNM-FH medium. The dish was rocked gently side to side to evenly distribute the cells. The cells were allowed to fully attach to the bottom of the dish to form a monolayer (about 50% confluence) for at least 15 minutes before performing transfection. In a 1.5 ml sterile microcentrifuge tube, the transfection mixture was set up with 4 $\mu$l (4 $\mu$g) of each of the transfer vector DNA (pBacJHcenv/S or pBacJhcenv/S-His), 10$\mu$l (1 $\mu$g) linearized Bac-N-Blue baculovirus DNA, 1 ml Grace's Insect media (without supplements, FBS, and antibiotics), and 20 $\mu$l insect liposomes (added last). The mixture was vortexed vigorously for 10 seconds, then incubated at room temperature for 15 minutes. While the transfection mixture was incubating, the TNM-FH media was removed from the cells carefully without disrupting the monolayer. The cells were rinsed twice with 2 ml Grace's Insect medium without supplements, FBS, and antibiotics. The transfection mixture was directly added onto the cell sheet dropwise, and evenly distributed over the monolayer. Following 4 hours incubation at 27° C., the cells was fed with 1 ml complete TNM-FH medium, placed in a sealed plastic bag, and incubated at 27° C. for 3 days. Blue plaque assay was used to select and purify the recombinant baculoviruses. The transfected cell culture medium (containing recombinant baculovirus) was collected and diluted to $10^{-2}$, $10^{-3}$, and $10^{-4}$ in 3 days post-transfection. Sf9 monolayer in 100 mm dish ($5\times10^6$ cells) was prepared (2–3 dishes for each viral dilution) in 5 ml complete TNM-FH medium. The confluence of the cells was about 50%. For viral infection, 3 ml medium was removed from the cells, 1 ml diluted virus was added dropwise. The virus was allowed to absorb to Sf9 cells at 27° C. for 1 hour. After completely removing the medium, the infected cell sheet was overlaid with 10 ml/dish baculovirus agarose [2.5 ml pre-warmed (at 47° C.) 2.5% agarose solution, and 2.5 ml pre-warmed complete TNM-FH medium, mixed with 5 ml complete TNM-FH medium with 150 $\mu$g/ml halogenated indolyl-b-D-galactosidase (blu-o-gal)]. The dishes were sealed in a plastic bag, and incubated at 27° C. until plaques form (about 3–5 days). Single blue plaque was picked up, and seeded into a 35 mm dish with $5\times10^5$ Sf9 cells in 2 ml complete TNM-FH medium. Three days post-inoculation, 0.75 ml cell suspension was harvested, the virus was precipitated with 20% polythylene glycol 8000 (PEG, in 1M sodium chloride), and the DNA was extracted with proteinase K digestion and phenol-chloroform extraction. The DNA was used to check the foreign gene (Hc1 env gene insertion and the purification of the recombinant virus by polymerase chain reaction (PCR). The positive plaques were propagated in Sf9 cells to prepare the high titer recombinant virus stocks.

EXAMPLE 7

Antigenic relationship between ADOL-Hc1, strain HPRS-103 and other subgroups of ALV.

In vitro neutralization tests were carried out to test antigenic relationship between ADOL-Hc1 and HPRS-103 viruses. Both ADOL-Hc1 and HPRS-103 were antigenically distinct from other subgroups (A–E). Strain HPRS-103, the prototype of ALV-J isolated from chickens in the United Kingdom, was neutralized by antibody to ADOL-Hc1, however, antibody to HPRS-103 did not neutralize ADOL-Hc1 virus (Table I). This finding suggests that both strains are antigenically related, but not identical, and documents the existence of antigenic variation among strains of ALV-J.

EXAMPLE 8

Immunoprecipitation.

The Hc1-infected cell lysates was performed with some modification for immunoprecipitation. Briefly, Sf-9 insect cells infected with recombinant baculovirus with Hc1 envelope insert were labeled with 35S-methionine for 5 hr at 48 hr post-infection. The labeled cells were treated with lysis buffer [25 mM Tris-HCl (pH 7.5), 150 mM NaCl, 0.1% Sodium dodecyl sulfate (SDS), 1% Triton X-100, 1% sodium deoxycholate] after rinsing once with PBS. Cell lysates were precleaned by incubation with 30 $\mu$l normal chicken serum (or 10 $\mu$l NS-1 ascites) and 50 $\mu$l protein A-Sepharose CL-4B (Pharmacia). The precleaned supernatants of cell lysates were immunoprecipitated with 30 $\mu$l chicken anti-Hc1 antiserum (or monoclonal antibody) and 50 $\mu$l protein A-Sepharose CL-4B. Samples were analyzed with 8% SDS-polyacrylamide gel electrophoresis (SDS-PAGE), followed by fluorography with 16% 2,5-Diphenyloxazile (PPO, SIGMA) in dimethyl sulfoxide (DMSO, J. T. Baker Inc.) and exposure on Kodak XAR-5 film. The result from immunoprecipitation study showed a major protein band with Mw between 80–90 kD from recombinant baculovirus-infected Sf-9 cells. This size of protein was higher than the calculated molecular weight from the amino acid sequence data (63 kD for overall size for env protein). This difference in molecular weight is expected because of the large numbers of potential N-glycosylation sites (17 sites) throughout the env protein molecule.

EXAMPLE 9

Indirect Immunofluorescence Assay (IFA).

CEF coverslips infected with different strains of ALV-J were fixed with 40% ethanol and 60% acetone, labeled with Hc1 anti-chicken antiserum at 1:100 dilution in phosphate buffer saline (PBS), pH 7.0 and goat anti-chicken IgG-FITC (1:100 in PBS). These samples were examined with a laser scanning confocal microscope (Carl Zeiss, Inc) with 40× oil lane, 488 argon laser line with green (BP520-650) barrier filter, fluorescence operation and confocal modes. The photographs were taken under the same conditions. Abundant expression of ALV-J Hc1 protein in the cytoplasm and surface of infected cells was observed. Same results were obtained from the Hc1 recombinant baculovirus-infected Sf-9 cells.

EXAMPLE 10

Induction of antibodies to env protein immunized with cells infected with baculovirus expression vector.

A group of 10 chickens was immunized with $10^6$ recombinant baculovirus-infected cells at day 1 of age. Three weeks after immunization, blood was obtained from these chickens and plasma was used to detect the presence of antibody to the env protein of ALV-J Hc1 in an ELISA test. Results indicated that all 10 chickens induced antibodies to the env protein.

EXAMPLE 11

Comparison of ELISA tests based on gp85 antigen of ALV-J Hc1 strain vs. RPRS 103 strain.

An ELISA test based on a gp85 recombinant protein preparation produced by the ALV-J Hc1 baculovirus expression vector described in Example 6 was compared to an ELISA test based on a similarly-prepared recombinant protein of the HPRS 103 strain. Forty SPF day old chickens were inoculated with ALV-J Hc1 virus by I/M route, and ten chicks served as a control. Sera were collected at 4 and 6 weeks post vaccination and tested for antibody. Hc1 gp85 ELISA detected 53% of chickens from the infected flock as positive, compared to only 27% detection with the HPRS-103 gp 85 ELISA. No positive reaction was observed in either ELISA plate using non-infected chicken sera. These results suggest that Hc1 gp85 recombinant antigen is more sensitive compared to HPRS-103 gp recombinant antigen for the detection of antibody to ALV-J Hc1 strain of virus infected chickens in ELISA.

TABLE I

Antigenic relationship between strains ADOL-Hc1 and HPRS-103 of ALV-J and other subgroups of ALV

| Antibody | ALV/Neutralization* | |
|---|---|---|
| | HPRS-103 | ADOL-Hc1 |
| A | – | – |
| B | – | – |
| C | – | – |
| D | – | – |
| E | – | – |
| HPRS-103 | + | – |
| ADOL-Hc1 | + | + |
| Control (negative) | – | – |

*(–) = no neutralization
(+) + neutralization observed

We claim:

1. An isolated nucleic acid molecule selected from the group consisting of RNA, cDNA, and double stranded DNA, wherein said molecule comprises a fragment encoding an envelope protein having the sequence of SEQ ID NO:2 and conservative substitutions thereof having a neutralization epitope such that antibody raised to said protein neutralizes both strains HPRS-103 and ADOL-Hc1 of avian leukosis virus subgroup J.

2. The molecule of claim 1, wherein said protein is the sequence of SEQ ID NO:2.

3. The molecule of claim 1, wherein said fragment is the sequence of SEQ ID NO:1.

4. An isolated nucleic acid molecule consisting of a sequence that is 98% identical to SEQ ID NO:1.

5. An immunogenic composition comprising the nucleic acid of claim 1 or an expression product thereof.

6. A vector selected from the group consisting of an expression vector and a cloning vector, wherein said vector comprises:

(1) a DNA molecule encoding an envelope protein having the sequence of SEQ ID NO:2 and conservative substitutions thereof having a neutralization epitope such that antibody raised to said protein neutralizes both strains HPRS-103 and ADOL-Hc1 of avian leukosis virus subgroup J, and (2) appropriate regulatory sequences for expression of said protein in a suitable host cell when said vector is an expression vector, or appropriate restriction enzyme sites and marker when said vector is a cloning vector.

7. The vector of claim 6, wherein said protein is the sequence of SEQ ID NO:2.

8. The vector of claim 6, wherein said vector is a baculovirus expression vector.

* * * * *